United States Patent
Wong et al.

(10) Patent No.: US 8,980,572 B2
(45) Date of Patent: Mar. 17, 2015

(54) METHODS OF SIGNAL GENERATION AND SIGNAL LOCALIZATION FOR IMPROVEMENT OF SIGNAL READABILITY IN SOLID PHASE BASED BIOASSAYS

(75) Inventors: Ling Wai Wong, Hong Kong (CN); Pui Yee Cangel Chan, Hong Kong (CN); Wing Cheung Mak, Hong Kong (CN); King Keung Sin, Hong Kong (CN); Reinhard Renneberg, Hong Kong (CN)

(73) Assignee: Supernova Diagnostics, Inc., Germantown, MD (US)

( * ) Notice: Subject to any disclaimer, the term of this patent is extended or adjusted under 35 U.S.C. 154(b) by 205 days.

(21) Appl. No.: 13/375,121

(22) PCT Filed: Jun. 14, 2010

(86) PCT No.: PCT/GB2010/001152
§ 371 (c)(1),
(2), (4) Date: Feb. 6, 2012

(87) PCT Pub. No.: WO2010/142963
PCT Pub. Date: Dec. 16, 2010

(65) Prior Publication Data
US 2012/0156693 A1 Jun. 21, 2012

(30) Foreign Application Priority Data
Jun. 12, 2009 (GB) .................................. 0910203.9

(51) Int. Cl.
*G01N 33/558* (2006.01)
*G01N 33/543* (2006.01)
(Continued)

(52) U.S. Cl.
CPC ........ *G01N 33/54393* (2013.01); *B01L 3/5055* (2013.01); *G01N 33/558* (2013.01);
(Continued)

(58) Field of Classification Search
CPC ............. B01L 9/527; B01L 2300/069; B01L 2300/0816; B01L 2300/0825; B01L 2300/0887; B01L 2400/0406; B01L 2300/043; B01L 3/5055; B01L 2300/046; B01L 2300/047; B01L 3/5023; B01L 2400/0457; B01L 9/52; G01N 33/558; G01N 21/78; G01N 31/22; G01N 33/54366; G01N 33/53; G01N 33/5302; G01N 33/536; G01N 33/537; G01N 33/543; G01N 33/54313; G01N 33/5432; G01N 33/559; G01N 33/561
USPC ........... 422/50, 400, 401, 408, 412, 420–429, 422/68.1, 69, 70, 82.05, 82.08, 554; 435/287.1, 287.2, 287.7, 287.8, 287.9; 436/514, 515, 518, 523, 165, 169, 170, 436/172
See application file for complete search history.

(56) References Cited

U.S. PATENT DOCUMENTS 5,071,746 A * 12/1991 Wilk et al. ..................... 435/7.94
5,468,648 A * 11/1995 Chandler ....................... 436/518
(Continued)

FOREIGN PATENT DOCUMENTS

EP    0 212 670 A2    3/1987
EP    1 309 867 B1    5/2003
(Continued)

OTHER PUBLICATIONS

Trau et al., *Analytical Chemistry*, vol. 74, No. 21, pp. 5480-5486 (2002).
(Continued)

*Primary Examiner* — Melanie Y Brown
*Assistant Examiner* — Erik B Crawford
(74) *Attorney, Agent, or Firm* — RatnerPrestia

(57) ABSTRACT

A method for generating and localizing a signal in a solid phase substrate detection system comprises applying a solution of target material to a substrate; binding the target with a specific affinity molecule having an attached label, the label comprising multiple signal precursor molecules; applying a carrier to the substrate, and treating the label to convert the signal precursor molecules to signal generating molecules. The carrier comprises solvent for the label and thickener for localizing the signal. The carrier may include developer that converts signal precursor molecules to signal generating molecules. Developer is not necessary if the signal precursor molecules are converted to signal generating molecules by e.g. temperature change, pH change, sonication, light irradiation, microwave heating. A test device for detecting target in a fluid sample, and a kit of parts for determining the presence of target in a fluid sample are also disclosed.

15 Claims, 6 Drawing Sheets

(51) Int. Cl.
*B01L 3/00* (2006.01)
*G01N 33/53* (2006.01)
*G01N 33/537* (2006.01)

(52) U.S. Cl.
CPC ........... *G01N 33/53* (2013.01); *G01N 33/5302* (2013.01); *G01N 33/537* (2013.01); *B01L 2300/069* (2013.01); *B01L 2300/0825* (2013.01); *B01L 2300/043* (2013.01); *B01L 2300/046* (2013.01); *B01L 2300/0816* (2013.01)

USPC .............. 435/7.9; 422/50; 422/400; 422/401; 422/408; 422/412; 422/420; 422/421; 422/422; 422/423; 422/424; 422/68.1; 422/69; 422/70; 422/82.05; 422/82.08; 422/554; 435/287.1; 435/287.2; 435/287.7; 435/287.8; 435/287.9; 436/514; 436/515; 436/518; 436/523; 436/165; 436/170; 436/172

(56) References Cited

U.S. PATENT DOCUMENTS

| | | | | |
|---|---|---|---|---|
| 5,879,951 | A * | 3/1999 | Sy | 436/514 |
| 5,939,252 | A * | 8/1999 | Lennon et al. | 435/4 |
| 7,442,557 | B1 * | 10/2008 | Clark et al. | 436/514 |
| 2003/0049866 | A1 | 3/2003 | Bushway et al. | |
| 2004/0253142 | A1 * | 12/2004 | Brewster et al. | 422/58 |
| 2005/0183494 | A1 * | 8/2005 | Tess et al. | 73/53.01 |
| 2005/0196318 | A1 * | 9/2005 | Matusewicz et al. | 422/58 |
| 2010/0282609 | A1 * | 11/2010 | Pollack et al. | 204/450 |

FOREIGN PATENT DOCUMENTS

| | | |
|---|---|---|
| WO | WO 02/12888 A2 | 2/2002 |
| WO | WO 2008/030546 A2 | 3/2008 |

OTHER PUBLICATIONS

PCT/GB2010/001152 International Search Report dated Mar. 9, 2010 by A. Adida of European Patent Office.

\* cited by examiner

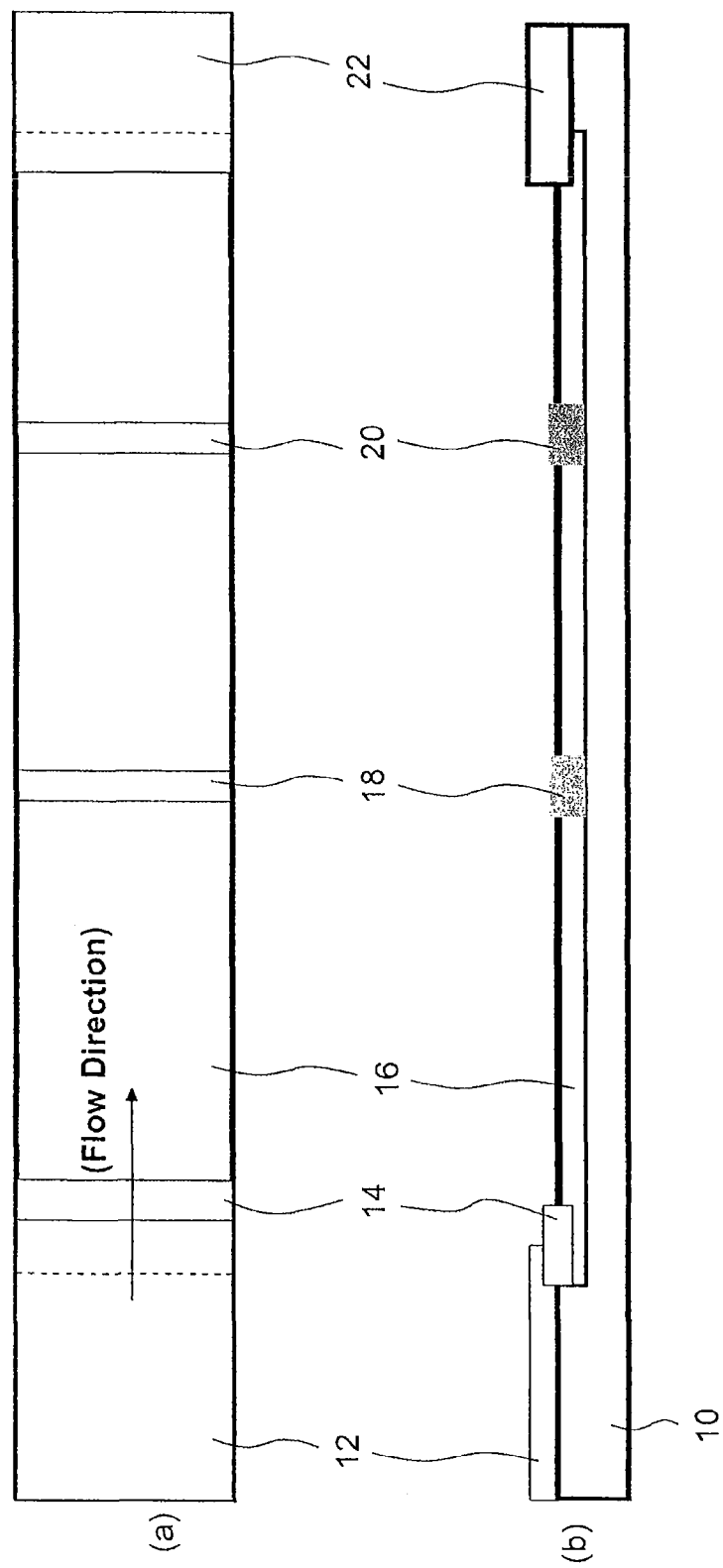

Figure 2 a) Direct Label → fine discrete, well-defined Test- and Control Lines: 18 and 20

| Sample | Antibody(1)-Colloidal gold | Antibody(2) | Goat-Anti-Mouse-Immunglobulin G | b) Amplified Label → diffuse, badly-defined Test- and Control Lines: 18 and 20

| Sample | Antibody(1) - Signal precursor | Antibody(2) | Goat-Anti-Mouse-Immunglobuline | y = amplified label, which diffuses driven by the wicking power of the absorbent pad

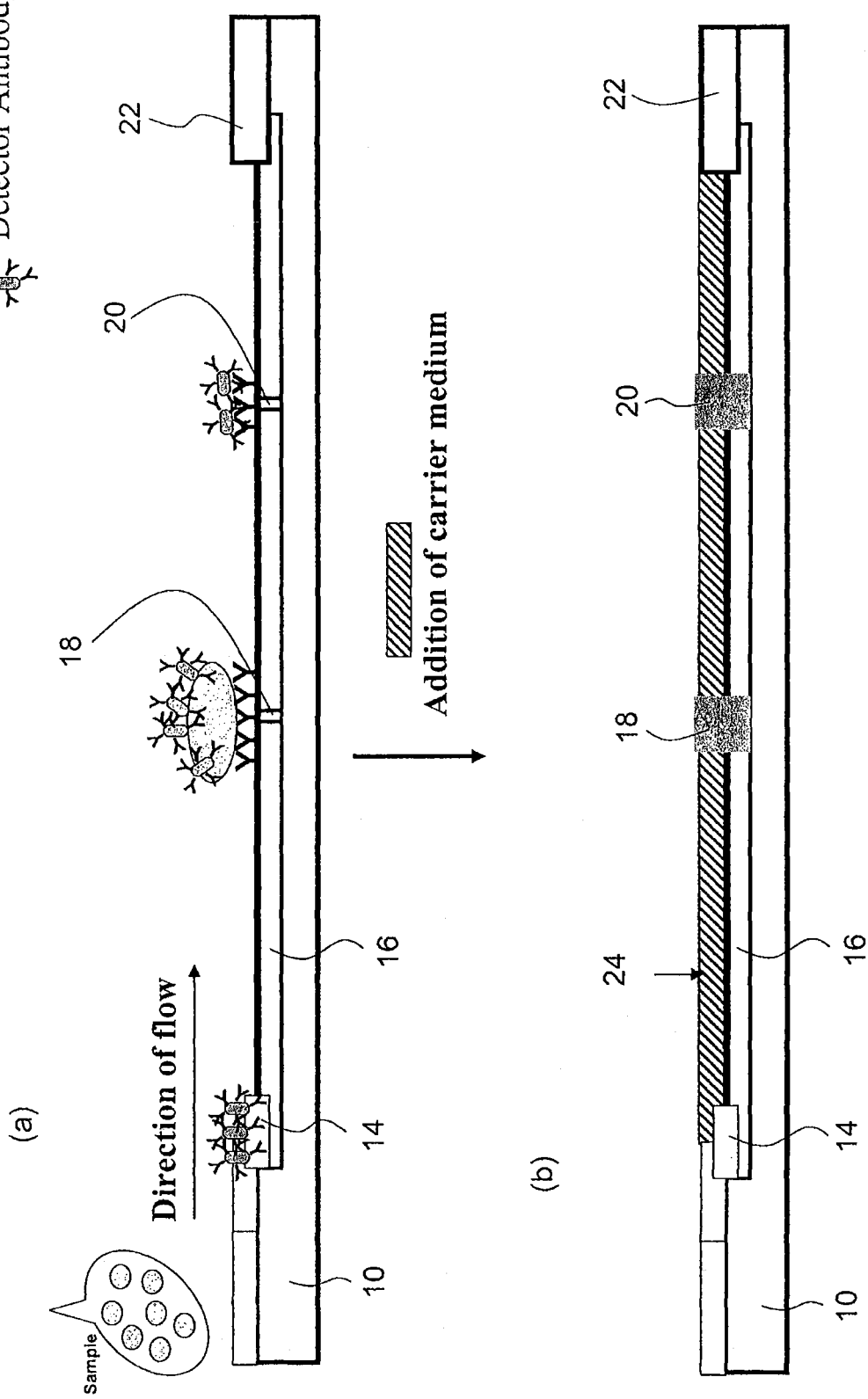

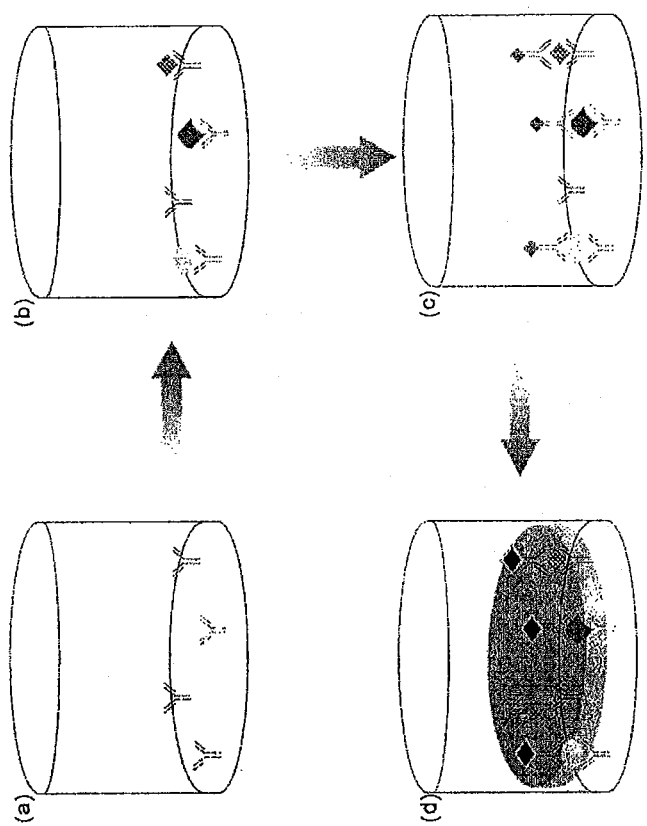
Figure 5 General Principle of the multiplex detection platform
(a) Different capture probes coated at design location
(b) Addition of multiple analytes
(c) Addition of FDA detectors
(d) Localize fluorescence signal generation

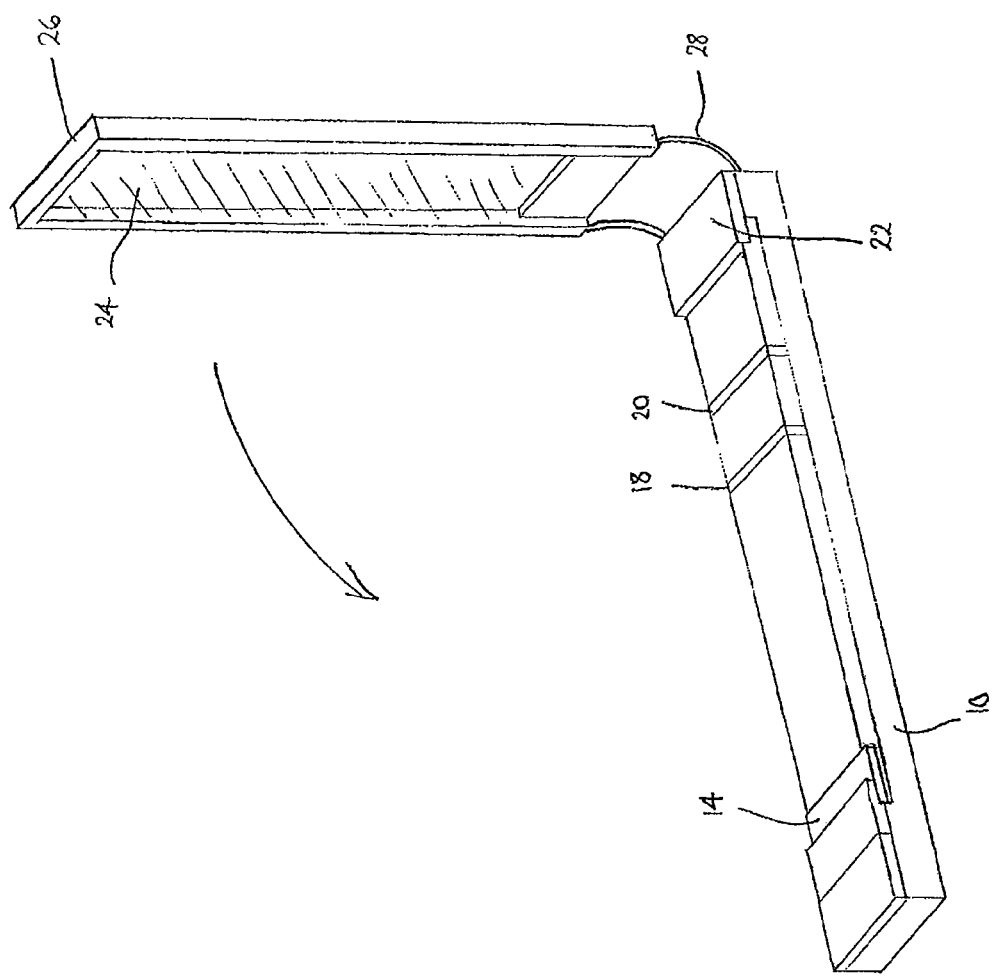

METHODS OF SIGNAL GENERATION AND SIGNAL LOCALIZATION FOR IMPROVEMENT OF SIGNAL READABILITY IN SOLID PHASE BASED BIOASSAYS

CROSS-REFERENCE TO RELATED APPLICATION

This application is a U.S. National Phase Application of PCT International Application PCT/GB2010/001152, filed Jun. 14, 2010 which claims priority benefit of Great Britain application number GB 0910203.9, filed Jun. 12, 2009, the contents of which are incorporated herein by reference in their entireties for all purposes.

FIELD OF THE INVENTION

The present invention relates to assays for analytes, e.g., antigens, in a liquid sample such as a body fluid. More particularly, the invention relates to a non-catalytic method for the detection of an analyte in a body fluid such as urine, blood, serum, plasma, saliva or an extraction solution of faeces using a conjugate comprising detectable material in a point of care (PoC) test device using a solid phase platform, such as a lateral flow device. The invention is also applicable to non-clinical situations, such as testing food and water for contaminants, or in the veterinary field or military.

BACKGROUND OF THE INVENTION

The invention uses a carrier medium to carry different reagents for signal generation and signal localization in the assay. The carrier medium comprises:
(i) Solvent (e.g., aqueous solution including buffer, salt solution, water; organic solvent, e.g., alcohols such as ethanol, propanol; ethers such as tetrahydrofuran (THF), and polar aprotic solvents such as dimethyl sulfoxide (DMSO);
(ii) Thickener, which dissolves in the solvent as a colloid mixture that forms an internal structure giving the resulting carrier medium properties ranging from those of a high viscosity fluid to a gel. Gel type carrier media have the appearance of a solid while being mostly composed of the solvent. Examples include polymers such as polyacrylamide and polyisobutylene; polysaccharides such as starches, cellulose, alginates obtained from brown algae, agar, carrageenan, pectin; natural gums such as locust bean gum and guar gum; proteins such as collagen, albumin and gelatin.

In some embodiments, the carrier medium may also include a signal developing reagent which is a material that converts signal precursor molecules to a state in which they generate a measurable signal. In other embodiments, a signal developing reagent is not necessary because the plurality of signal precursor molecules is converted to a plurality of detectable signal molecules by physical means such as change in temperature, change of pH, sonication, light irradiation or microwave heating.

The functions of the carrier medium are:
(i) To hinder the diffusion of the signal molecules, leading to signal accumulation.
(ii) To improve the readability (sharpness, prolongation of signal retention time) of the signal on the solid phase platform, and thus enhance the sensitivity.

In some embodiments, where the conversion of the plurality of signal precursor molecules to a plurality of detectable signal generating molecules is brought about by chemical or biochemical means, the carrier medium has a third function:
(iii) To generate a signal by converting a plurality of signal precursor molecules to a plurality of detectable signal generating molecules.

For assays using detection of visible light, the carrier medium is substantially optically transparent.

Many types of target-receptor assays have been used to detect the presence of various target substances in body fluids such as urine, blood, serum, plasma, saliva or extraction solutions of faeces. These assays typically involve antigen antibody reactions, synthetic conjugates with radioactive, enzymatic, fluorescent, luminescent, chemiluminescent, or visually observable metal tags, and use specially designed reaction chambers. In all such assays, there is a receptor, e.g., an antibody, which is specific for the selected target, e.g., antigen, and a means for detecting the presence, and often the amount, of the target-receptor reaction product. Many current tests are designed to provide a semi-quantitative or quantitative determination but, in many circumstances, all that is required is a qualitative detection providing a positive or negative indication of the presence of the target species. Examples of such qualitative assays include blood typing, most types of urinalysis and the very important faecal occult blood test as a screening assay for colorectal carcinoma. For these tests, visually observable indicia such as the accumulation of coloured particles, e.g., gold particles, the presence of agglutination or a colour change are preferred.

Nevertheless, qualitative assays must be very sensitive because of the often small concentration of the target of interest in the test fluid. Sandwich assays and other sensitive detection methods which use metal sols or other types of coloured particles have been developed. However, these techniques have not solved all of the problems encountered in rapid detection methods and further improvements are constantly being sought.

By way of example, in lateral flow sandwich assays, colloidal gold is often used as a label of a first antibody (1) whereas the other antibody (2) is fixed in a well-defined detection site on a membrane such as a nitrocellulose membrane. If the analyte in question is present in a sample, then the analyte reacts with the gold labelled antibody (1) and migrates to the nitrocellulose membrane-bound antibody (2). There it forms a sandwich and these sandwich complexes are then collected and concentrated in the detection site. This zone can be made more visible to a certain extent (amplified) by additional reaction with silver ions.

However, the analytical sensitivity is not outstanding and this technology is not readily applicable to certain assays, e.g., for the determination of thyroid-stimulating hormone (TSH), prostate specific antigen (PSA), Troponin I or Troponin T in the low—but diagnostically very important—concentration range.

Therefore, in order to make such assays more effective, other labels are used (named "signal amplification precursor molecules") which can be amplified at the end of the determination reaction, for example at the end of the formation of the sandwich: antibody $(2)_{fixed}$-analyte-{antibody (1)-label}.

If the amplification label is a microcapsule containing crystalline fluorescein diacetate (FDA)—consisting of millions of FDA molecules—then the amplification is effected after the determination reaction by disintegrating the microcapsule and hydrolysing the non-fluorescing FDA-molecules to fluorescing fluorescein molecules. This amplification is well proven and described in granted European patent number EP 1309867, the disclosure of which is incorporated herein by reference.

Normally the amplification reaction takes place in a solution of the releasing reagent. This leads to a slight decrease in analytical sensitivity from the ideal because of the dilution factor—the released fluorescein molecules become diluted in the reaction volume of the releasing reagent.

Unfortunately, in certain circumstances, the benefit of amplification can be offset or even outweighed by the disadvantage of signal dissipation. For example, if the detection or determination is performed on a membrane, e.g., in a lateral flow test strip, the addition of a solution of releasing reagent for enabling signal amplification results in diffusion of the amplified signal along the membrane. The released/amplified molecules are not localized and hence the signal may be difficult to detect even after amplification. The addition of any solution—after the underlying test reaction has been completed—leads to an enlargement of the detection line, spot or zone. Diffusion broadens the detection site and it is not possible to measure reliably the colour intensity of the detection site.

The prior art also includes examples where the label may be an enzyme with a high turnover number which, when it reacts with its substrate, forms very many reaction product molecules. Again, this is carried out in aqueous solution, more specifically in a buffer solution with the specific substrate molecules for the enzyme. One disadvantage of enzyme-based systems is that, because they are catalytic, the amplification starts when the conversion of the substrate occurs and this is an ongoing process. The amplification is dependent on the substrate concentration and on the time chosen for the enzymatic reaction. If no stopping reagent is added, the enzyme will work during the measurement time (and afterwards), so there is not a constant signal. Addition of a stopping agent will increase the dilution effect.

SUMMARY OF THE INVENTION

It is therefore an object of the invention to overcome limitations in state-of-the-art technology by hindering diffusion of signal molecules and thereby improve the readability of the signal by maintaining its sharpness and prolonging the signal retention time so that amplified signals can be detected reliably. It is also an object of the invention to provide a rapid, sensitive method for detecting analytes in fluid samples, particularly samples of body fluids. Another object is to provide an assay which has high sensitivity compared to conventional assays. A further object is to provide a test device for detection of low levels of analytes in fluids.

DEFINITIONS

Carrier medium: The carrier medium hinders diffusion of the molecules providing the amplified signal, leading to signal accumulation. This results in improved readability (sharpness, prolongation of signal retention time) of the amplified signal on the solid phase platform, and thus enhances the sensitivity.

The carrier medium comprises:
 (i) Solvent (e.g., aqueous solution including buffer, salt solution, water; organic solvent, e.g., alcohols such as ethanol, propanol; ethers such as tetrahydrofuran (THF), and polar aprotic solvents such as dimethyl sulfoxide (DMSO);
 (ii) Thickener, which dissolves in the solvent as a colloid mixture that forms an internal structure giving the resulting carrier medium properties ranging from those of a high viscosity fluid to a gel.

The carrier medium may also comprise, for signal precursor molecules requiring chemical or biochemical activation:
 (iii) Signal developing reagent, which is a material that converts signal precursor molecules to a state in which they generate a measurable signal.

Thickeners: These are materials used to thicken and to stabilize liquid solutions, emulsions, and suspensions. They dissolve in the liquid phase as a colloid mixture that forms an internal structure giving the resulting carrier medium properties ranging from those of a high viscosity fluid to a gel. Gel type carrier media have the appearance of a solid, while being mostly composed of a liquid. Examples of thickeners include gel-forming polymers such as polyacrylamide and polyisobutylene; polysaccharides such as cellulose, starches, alginates obtained from brown algae, agar, carrageenan, pectin; natural gums such as locust bean gum and guar gum; proteins such as collagen, albumin and gelatin.

Signal precursor molecules: These are molecules which, when reacted with one or more other reagents, lead to a measurable signal. There are very many different substances from different chemical classes which lead via an initiated reaction to a measuring signal, for example fluorophores and their derivatives, luminophores and their derivatives, chromophores and their derivatives, prosthetic groups, or redox active substances selected from redox mediators, electrode-active substances, bioluminogenic and fluorogenic proteins, visible dyes, fluorescent dyes, bioluminescent or chemiluminescent materials, electrochemically active materials, or magnetic materials. The signal precursor molecules are non-catalytic labels.

The measurable signal can be based on:
fluorimetry
luminometry
colour change in the ultraviolet, visible and near infrared range
change in redox-potential.
change in mass resulting from complex formation or precipitation
detection of radioactive decay products
detection of magnetic field Signal molecules: The term signal molecules is used in this specification to denote both signal precursor molecules and/or signal generating molecules where the context does not require them to be in a particular one of the signal precursor state or the signal generating state. It is also used where signal precursor molecules and signal generating molecules may both be present together at the same time.

Signal developing reagent: The signal developing reagent, if present, is a material that enables signal precursor molecules to generate a measurable signal. The signal developing reagent may be adapted to activate fluorophores selected from the group consisting of fluoresceins and their derivatives, including fluorescein diacetate (FDA), fluorescein diacetate isothiocyanate (FDA-isothiocyanate) or fluorescein diacetate maleimide (FDA-maleimide), cyanines, carbocyanines, rhodamines, xanthenes, diazo-dye based fluorescent substances, and small fluorescent aromatic and heteroaromatic molecules. Alternatively, the signal developing reagent may activate chromophores selected from the group consisting of cyanine, pyrazolone, anthraquinone, carbocyanine, rhodamine, xanthen, carotenoid and diazo- and monoazo, oxazine, indigoid, or riboflavine based dye substances.

Test device: As used in this document, the term test device is used to denote a device which incorporates a solid phase substrate. The solid-phase substrate may be selected from the group consisting of a membrane, a microtitre plate, beads (magnetic and non-magnetic), tubes and slides. The test device may be adapted to different formats of assay, including lateral flow, vertical flow, test tubes, microtitre plate, petal, etc. The material and form for the solid-phase substrate may be: a porous membrane such as nitrocellulose, nylon; a non-porous flat surface such as glass, polystyrene, metal, carbon; the inner wall of a test tube or a microtitre plate; spheres such as magnetic or non-magnetic beads.

Detection membrane: A detection membrane is composed of a reaction membrane, e.g. a nitrocellulose strip to which different pads—some with reagents—are attached (e.g., conjugate pad, sample pad, absorbent pad). Reaction sites (detection site, control zone) with antibodies or antigens are coated at well defined locations on the reaction membrane. The coatings at the reaction sites may be passively adsorbed onto the reaction membrane, they may be covalently bound, or they may be bound immuno-chemically, e.g., via streptavidin (streptavidin coated←biotinylated antibody) or via a species-specific antibody (goat anti-mouse-antibody←mouse-antibody).

Affinity molecules: The affinity molecules may be biorecognition molecules selected from the following groups of materials:
  (a) peptides or proteins selected from the group consisting of antibodies, monoclonal antibodies, polyclonal antibodies, receptors, antigens, lectins, avidins, oligopeptides, lipoproteins, glycoproteins, peptide hormones and allergens or parts thereof;
  (b) nucleic acids selected from the group consisting of DNA, RNAs, oligonucleotides, aptamers and parts thereof;
  (c) carbohydrates selected from the group consisting of mono-, oligo- and polysaccharides, glycolipids, proteopolysaccharides and parts thereof; or
  (d) low molecular weight ligands selected from the group consisting of biotin, biotin derivatives, steroids, hormones, cofactors, activators, inhibitors, drugs, allergens or haptens.

Target: The term "target" is used in the present specification to mean both the analyte in a sandwich type assay, or the competitor in a competitive type assay.

BRIEF DESCRIPTION OF THE DRAWINGS

The invention will now be described by way of example only and without limitation with reference to the drawings in which:

FIG. 1 is a schematic view showing the construction of a known lateral flow test strip;

FIG. 2 schematically shows two views of a lateral flow test strip under use; view (a) illustrates a test strip using an unamplified label, whilst view (b) illustrates a test strip using a prior art solution technique to amplify the label;

FIG. 3 is another schematic illustration of a test strip showing the application of a thin film of carrier medium for localizing signal in accordance with the present invention;

FIG. 5 is a schematic illustration of a multiplex detection platform, and

FIG. 6 is a schematic illustration of a test strip having an optically transparent lid loaded with a matrix gel for placement over the test strip after completion of the determination reaction for effecting amplification of the visible signal.

DETAILED DESCRIPTION OF THE INVENTION

Figure 4:
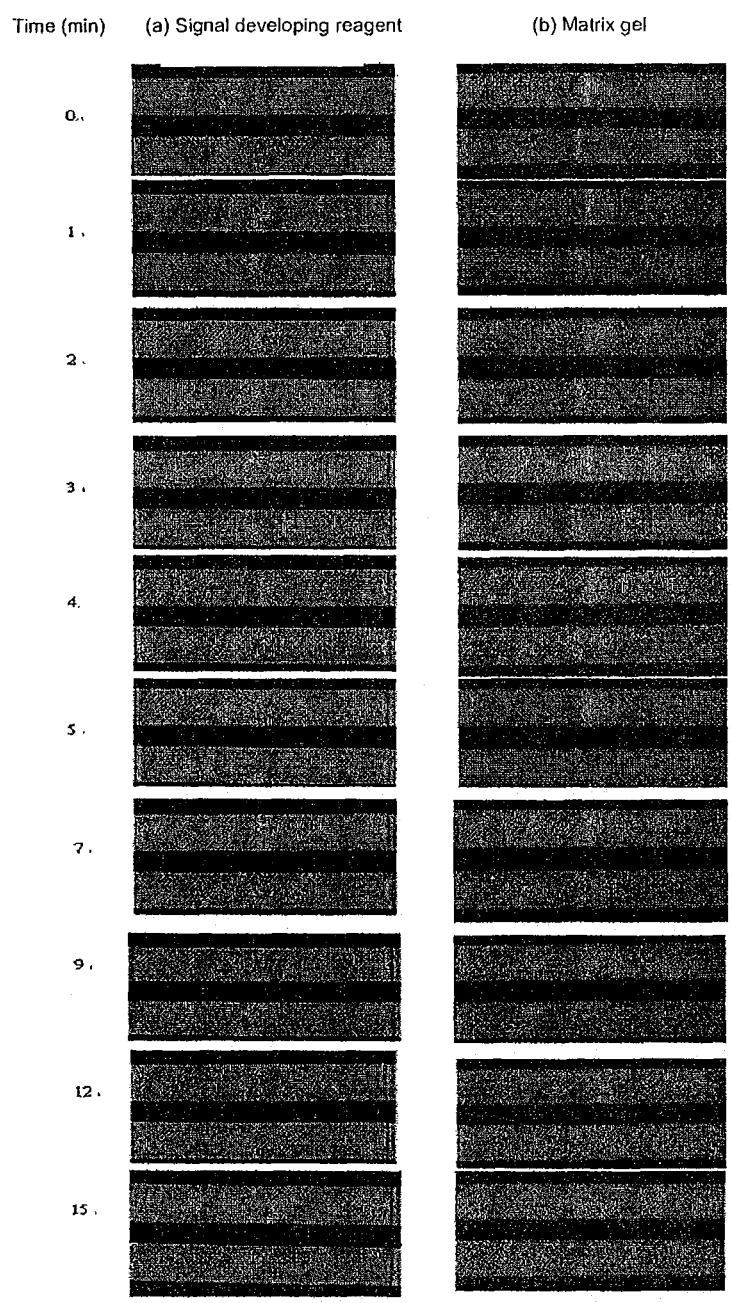
FIG. 4 illustrates the changes of fluorescent signal at different time intervals for signals amplified using a releasing solution (left-hand strips) and signals amplified using a matrix gel according to the present invention (right-hand strips)

The invention provides a method for generating and localizing a signal in a solid phase substrate detection system, said method comprising: applying a solution of a target material to a solid-phase substrate; binding said target material with a specific affinity molecule for that target material to which a non-catalytic label is attached, said non-catalytic label comprising a plurality of signal precursor molecules; applying a carrier medium to said solid phase substrate, and treating the label to convert the plurality of signal precursor molecules to a plurality of detectable signal generating molecules, wherein the carrier medium comprises a solvent for the dissolution of the non-catalytic label and a thickener for causing localization of the signal generated by the plurality of detectable signal generating molecules indicating the presence and/or quantity of said target.

In some embodiments, the carrier medium may also include a signal developing reagent which is a material that converts signal precursor molecules to a state in which they generate a measurable signal. In these embodiments, signal generation and signal localization occur simultaneously.

In other embodiments, a signal developing reagent is not necessary because the signal molecules are converted from the signal precursor state to the signal generating state by physical means such as change in temperature, change of pH, sonication, light irradiation or microwave heating. Preferably, the steps of applying the carrier medium to the solid-phase substrate and of treating the label to convert the plurality of signal precursor molecules to a plurality of detectable signal generating molecules are carried out substantially simultaneously. In practice, there may be a brief interruption of the treatment step to apply the carrier medium to the solid-phase substrate, or there may be a slight delay in commencing the treatment step after applying carrier medium.

The carrier medium may be applied to the solid-phase substrate in a number of different ways. It may be in the form of a matrix gel which may be applied directly as a thin film. Alternatively, the matrix gel may be separated from the solid-phase substrate by a protective layer which is removed when it is desired to bring the solid-phase substrate and the matrix gel into contact. If the carrier medium is liquid, it may be applied by spraying. Another alternative is dipping of the solid-phase substrate into the carrier medium or dropping carrier medium onto the solid phase substrate. Yet another alternative is immersion of the solid-phase substrate into a high viscosity liquid or matrix gel in a container.

In a second aspect, the invention provides a test device for detecting a target material in a fluid sample, said device comprising:

a solid-phase substrate detection system comprising means for transporting the fluid sample from a sample application site to a detection site;

disposed at a position remote from said detection site, a specific affinity molecule for that target material to which a non-catalytic label is attached, said non-catalytic label comprising a plurality of signal precursor molecules, said signal precursor molecules being convertible to a plurality of detectable signal generating molecules;

a carrier medium comprising a solvent for the signal molecules and a thickener for causing localization of signal generated by said plurality of detectable signal generating molecules at said detection site indicating the presence and/or quantity of said target material, and means for converting said plurality of signal precursor molecules to said plurality of detectable signal generating molecules;

wherein said carrier medium is adapted to be brought into contact with said detectable material at least at said detection site.

In some embodiments, the carrier medium may also include a signal developing reagent which is a material that converts signal precursor molecules to a state in which they generate a measurable signal. In other embodiments, a signal developing reagent is not necessary because the signal precursor molecules are converted to the signal generating state by physical means such as change in temperature, change of pH, sonication, light irradiation or microwave heating.

The invention further provides a kit of parts for determining the presence of a target material in a fluid sample, said kit comprising:

a solid-phase substrate detection system comprising means for transporting the fluid sample from a sample application site to a detection site;

disposed at a position remote from said detection site, a specific affinity molecule for that target material to which a non-catalytic label is attached, said non-catalytic label comprising a plurality of signal precursor molecules, said signal precursor molecules being convertible to a plurality of detectable signal generating molecules, and means for converting said plurality of signal precursor molecules to said plurality of detectable signal generating molecules.

The kit may further comprise ingredients for forming a carrier medium comprising a solvent and a thickener for causing localization of an amplified signal generated by said plurality of detectable signal generating molecules at said detection site. The means for converting the plurality of signal precursor molecules to the plurality of detectable signal generating molecules may be a signal developing reagent for inclusion in the carrier medium. The signal precursor material in the kit may comprise fluorophores and their derivatives, luminophores and their derivatives, chromophores and their derivatives, prosthetic groups, or redox active substances selected from redox mediators, electrode-active substances, bioluminogenic and fluorogenic proteins, visible dyes, fluorescent dyes, bioluminescent or chemiluminescent materials, or magnetic materials.

For the avoidance of doubt, the phrase non-catalytic also includes non-enzymic, the invention being based on the use of signal precursor material that comprises a plurality of signal precursor molecules that are convertible to a plurality of detectable signal generating molecules. Accordingly, when the target material becomes bound with a non-catalytic label having specific affinity for the target material, which non-catalytic label comprises a signal precursor material comprising a plurality of signal precursor molecules, there is an inherent or potential amplification of the detectable signal because each target molecule becomes associated with a plurality of signal precursor molecules. In other words, when the determination reaction has taken place, the signal precursor material can be "activated" and converted to a plurality of detectable signal generating molecules.

For example, consider the case where the target material is an antigen and the non-catalytic label conjugated with affinity molecules that specifically bind to the target material is a detector antibody bound to a micro-capsule containing a crystal of fluorescein diacetate (FDA, i.e., a crystal of signal precursor molecules). When the antigen/detector antibody is captured at a detection site (for example, by a capture antibody on a solid support), dissolution of the FDA crystal by a solvent and conversion of the FDA to fluorescein (by treatment with KOH, for example) releases millions upon millions of fluorescent molecules for each target antigen.

The invention provides a technical solution to the problem of line, dot, spot or zone broadening at a detection site and leads to an improvement of the readability of test and control lines especially in PoC test devices. The broadening is normally provoked and initialized by the addition of the required releasing or amplification reagents in aqueous solution. The detection site is not a sharp reaction line and becomes blurred, spread out and indefinite through the diffusion of substances in solution. By means of the present invention, the need to localize the signal at its place of formation is now satisfied.

In the description which follows, relative spatial terms such as "back", "left", "right", etc., are used for the convenience of the skilled reader and refer to the orientation of test devices and their constituent parts as depicted in the drawings. No limitation is intended by use of these terms, either in use of the invention, during its manufacture, shipment, custody, or sale, or during assembly of its constituent parts or when incorporated into or combined with other apparatus.

FIG. 1 is a schematic diagram showing a conventional lateral flow test strip in plan view (view (a)) and side view (view (b)). Reference numeral 10 denotes a back laminate for holding the porous components together. On top of this is seated a sample loading pad 12 where the sample is applied, in use. Next to this is a conjugate pad 14 which contains the detector material or probe that reacts with the target as this passes along the test strip in a fluid sample carried by the nitrocellulose membrane 16. In the flow direction from left to right as depicted in the figure, detection site 18 is a line of capture probe applied across the width of the test strip where the target/detector complexes are captured, whilst control zone 20 is a further line of material applied across the width of the test strip downstream from the detection site 18. The control zone does not detect anything in the sample, but indicates that the strip has been wetted correctly and that all of the test components are functional. The control zone should always produce a visible signal to verify that the test has been performed correctly, even for samples which do not contain any detectable target and therefore give rise to no signal in the detection site. The excess fluid is absorbed by sucking pad 22.

Turning now to FIG. 2, this shows in schematic form views of two lateral flow test strips under use. In view (a), a test strip is illustrated using a direct label, where there is no requirement to convert signal precursor molecules to signal generating molecules; the detection lines at the detection site and the control site are both sharp and well defined. View (b) is an illustration of a test strip in which, after the determination reaction has taken place, a solution of signal developing reagent has been added to initiate the conversion of signal precursor molecules to detectable signal generating molecules. Here, the detection lines at the detection site and the control site are not well defined; they have spread out due to diffusion of the signal generating molecules through the solution used to apply the signal developing reagent.

In the present invention, such diffusion is hindered. It enables conversion of signal precursor molecules to detectable signal generating molecules to be carried out whilst maintaining well-defined detection lines at the detection site and the control site. This is achieved by using a carrier medium which minimises the diffusion and distribution of the signal molecules. In some embodiments, the carrier medium may include a signal developing reagent that converts signal precursor molecules to detectable signal generating molecules, but the carrier medium is not in a form that allows rapid diffusion through the detection membrane.

The carrier medium is based on the development of a thickener with "matrix-bound water" in which a solvent and, in some embodiments also a signal developing reagent, have been dissolved in the sol state before the gel state is formed. In the gel state, the matrix minimises diffusion of the signal molecules supported on the detection membrane.

FIG. 3 is another schematic illustration of a test strip like the strip depicted in FIG. 1, where view (b) shows the application of a thin layer of carrier medium 24 to the upper surface of the detection membrane 16 for causing the generation of signal by converting a plurality of signal precursor molecules to a plurality of detectable signal generating molecules and localizing the plurality of detectable signal generating molecules in accordance with the present invention. Conveniently, the carrier medium may be a matrix gel which has been cut into a thin strip of film that is preferably matched in size to the exposed upper surface of the detection membrane.

FIG. 4 is a photograph illustrating the changes of fluorescent signal at different time intervals for signals generated using a conventional releasing solution (left-hand strips) and signals generated using a carrier medium containing a signal developing reagent in the form of a matrix gel (right-hand strips). Pairs of strips were photographed immediately after applying a conventional releasing solution to release fluorescein from the fluorescein diacetate signal precursor molecules or immediately after applying a matrix gel in accordance with the invention. The same pairs of strips were then photographed again at the following successive time intervals: 1, 2, 3, 4, 5, 7, 9, 12 and 15 minutes. The strips where the signal was generated using the matrix gel maintained well-defined lines even after 15 minutes, whereas the strips where the signal was generated conventionally using a releasing solution began to show signs of diffusion even at the first interval. After 15 minutes, these conventional strips showed very diffuse lines that would be virtually impossible to read reproducibly in practice.

Turning now to FIG. 5, this is a schematic illustration of how the matrix gel embodiment can be applied to a multiplex detection platform. In view (a), there is shown an optically transparent vessel having different capture probes coated at predetermined locations; the different capture probes are specific for certain targets. In view (b), the capture probes are exposed to a sample containing multiple targets which become bound to specific ones of the capture probes. In view (c), the bound targets are further reacted with biolabels having FDA signal precursor molecules. In view (d), a matrix gel having a signal developing reagent for the FDA is added to the container and localized fluorescence signals are generated at the sites where the targets became bound to respective capture probes.

FIG. 6 is a schematic illustration of a test strip having an optically transparent lid 26 loaded with a matrix gel 24 for placement over the test strip after completion of the determination reaction for effecting amplification of the visible signal. The lid may be a separate item, but is shown here attached by means of a living hinge 28 to the back laminate 10 supporting the porous components.

The present invention addresses the following problems and limitations of existing methods:

The fluorescence, luminescence or absorbance cannot be determined reliably because diffusion of the signal generating molecules means that measurement cannot be focused on the measurement area.

A decrease in analytical sensitivity occurs. The diffusion means that the fluorescence, luminescence or absorbance is not fixed in a well-defined zone but is distributed instead, over parts of the membrane that are not intended to be detection sites. This leads to a loss of detectable signal generating molecules by flux from their place of formation and therefore a decrease in analytical sensitivity occurs.

If the lateral flow device is conceived as a semi-quantitative one, then several antibody (2) lines are provided on the membrane. The result cannot be interpreted because the detectable signal generating molecules are blurred/distributed between and after the lines.

The invention addresses these problems based on a modification of the viscosity term of the diffusion coefficient of Fick's well-known first and second laws dealing with diffusive flux. Fick postulated that the flux proceeds from regions of high concentration to regions of low concentration, with a magnitude that is proportional to the concentration gradient (dc/dx). In one spatial dimension, the equation is:

$$J = -D^*(dc/dx)$$

where

J is the diffusion flux which is a measure of the amount of substance that will flow through a small area during a short time interval. In the present invention, it is desirable for the value of J to be a minimum.

D is the diffusion coefficient in "bound" gel-water dependent on the pore sizes, their distribution and especially on the viscosity of the "liquid".

c is the concentration; here, for example, of the formed fluorescein.

x is the position or distance from the location of formation; here the distance from the detection site.

The diffusion coefficient (D) is proportional to the squared velocity of the diffusing particles, which depends on the temperature, viscosity of the fluid and the size of the particles. In dilute aqueous solutions, the diffusion coefficients of most ions are similar and have values that typically range from $0.6 \times 10^{-9}$ to $2 \times 10^{-9}$ m$^2$/s. For biological molecules, diffusion coefficients normally range from $10^{-11}$ to $10^{-10}$ m$^2$/s.

The invention uses a carrier medium incorporating the reagents necessary for localization of the signal molecules. As previously discussed, in some embodiments the carrier medium may also include a signal developing reagent for converting signal precursor molecules to detectable signal generating molecules. In other embodiments, this conversion is achieved by physical means such as change in temperature, change of pH, sonication, light irradiation or microwave heating. In the case of an aqueous gel, the water is tightly bound/fixed in the matrix of the gel, after the gel state has been formed from its sol state. Diffusion becomes noticeably impeded because the liquid (water) in the gel is more or less "solidified". In the case of a liquid with a high shear modulus, the solvent impedes diffusion of the signal molecules.

Gels containing the key reagents can be easily produced by dissolving the reagents in the sol state of the gel forming compound. After incorporation of the reagents into the sol, the sol is transformed to the gel state after a certain amount of time or the transformation may be induced by a temperature change (e.g., Agar-Agar is liquid (sol state) at higher temperatures and solid (gel state) at lower temperatures.

There are numerous substances which occur in both a sol and a gel state. The gel and sol state with water can be characterized in that, in the sol state, the gel-forming substance—the thickener—is colloidally dispersed in water whereas, in the gel state, the water is dispersed in the gel-forming network of the thickener.

In one particular preferred embodiment, the invention makes use of the amplification principle disclosed in European patent no. EP 1309867, in which the label of one reaction partner is a FDA crystal incorporating millions of non-fluorescing FDA-molecules. These become hydrolysed at the reaction zone to millions of fluorescein molecules. By virtue of the thickener incorporated in the carrier medium, the thus-formed fluorescein molecules are hindered from diffusing away from the reaction site.

In this process, DMSO and NaOH are the solvent and signal developing reagent which are incorporated into the carrier medium. The signal localization effect is explained by the partial diffusion of the DMSO and NaOH out of the carrier medium (i.e., flux from a region of high concentration of DMSO and NaOH solution to a region of lower concentration) to the surface of the detection membrane. FDA-crystals dissolve in the DMSO and are hydrolysed by NaOH to fluorescein, which fluoresces. Because the water is strongly bound in the carrier medium, which may be considered as a cross-linked, 3-dimensional network by virtue of the action of the thickener, small molecular weight substances only diffuse through the carrier medium with the bound aqueous water and come quickly into contact with the detection membrane. This process does not take longer than about 30 seconds.

Because no aqueous solution having unbound water is added, no diffusion and distribution—assisted by the absorbent pad of the detection membrane—of the fluorescein molecules occurs. Hence, the fluorescein molecules are localized and can be measured without losing analytical sensitivity. Also there is no curtailment of the readability if further detection lines in semi-quantitative determinations are present.

For certain detection platforms, the carrier medium can be in the form of a matrix gel produced as a large thin sheet which is then cut into suitably sized pieces for placement on the detection membrane. In feasibility studies this placement was performed using forceps.

Another approach is to integrate the carrier medium into a separate transparent cover device which is adapted to bring the carrier medium into contact with the detection membrane when it is closed after completion of the determination reaction. In this case, the detection device consists of two pieces in the form of a box. The detection device (box) is opened, the determination reaction is performed on the lower part of the box with the detection membrane. Subsequently the box is closed with the cover in which the carrier medium is integrated. To prevent inadvertent contact between the signal precursor molecules and the carrier medium due to premature closure of the cover, the carrier medium may have a protective cover of a thin sheet of releasable film that is removed after the determination reaction has been carried out. Only then can the carrier medium contact the detection sites on the detection membrane.

Preparation/Production of the Carrier Medium

The formation of the carrier medium can be performed generally by the mixing of the solvent, signal developing reagent (if present) and thickener. Heating and cooling may be required depending on the choices of thickener.

Different thickeners or mixtures of thickener may be used for the carrier medium forming process. For each type of thickener, the appropriate concentrations for the thickeners to achieve localization of the detectable signal generating molecules have to be optimised regarding bound water content, shear characteristics of the gel, shrinking during the solidification process, diffusion constant of the integrated reaction partners, densification, optical transparency, stability, and robustness to temperature changes.

The viscosity of the carrier medium when in the form of a matrix gel may be compared to that of polyacrylamide gels used in SDS-PAGE. A low percentage gel, which would not be very thick, may be applied to the surface of the detection membrane by spraying. A high percentage thick gel is more suited to certain multiplex detection platforms where coated petals are immersed in a gel to develop an amplified signal.

The percentage of gel may range from 0.05 to 50% by weight based on the total weight of the medium; more preferably in range of 0.1% to 20%. In other embodiments, the lower limit for the proportion of the gel may have any one of the values 0.05%, 0.1%, 0.2%, 0.3%, 0.4% and 0.5%; the upper limit for the proportion of the gel may have any one of the values 3%, 4%, 5%, 10%, 20% and 50%. Ranges for the proportion of the gel may therefore be a combination of any of the aforementioned lower limits with any of the aforementioned upper limits.

The shear modulus of the carrier medium can be tuned by varying the amount of thickener added. Of course, a solution with high viscosity can also slow down the diffusion but the signal retention time will be shorter than that obtained using the solidified form.

If the matrix gel is optimised, localized reaction lines (signal lines) at the position of the detection site are obtained, as shown in FIG. 4 based on experimental results. FIG. 4 shows once more the remarkable differences in the shape of the detection sites if the matrix gel is used for signal generation and signal localization, rather than an aqueous solution.

EXAMPLES

The invention will now be particularly described with reference to various examples, although it is understood that these are non-limiting.

Example 1

Preparation of the DMSO-Based Carrier Medium for the Initiation of FDA-Crystal Amplification Procedure The carrier medium for FDA is composed of DMSO, NaOH and Polysorbate 20, in which the purpose of the DMSO is to dissolve the FDA and NaOH is used to hydrolyse the dissolved FDA. Polysorbate 20 is the active component for gel formation. Specifically, the constituents are mixed together (e.g., mixing 1 ml of DMSO+1 ml of 1M NaOH+50 µl of Polysorbate 20) and left to stand at room temperature for 5-10 minutes for solidification.

Table 1 shows the optimisation of the compositions and of the appearance of certain carrier media in the form of matrix gels.

TABLE 1

Compositions and appearances of matrix gels

| Name | Tween 20* | SDS 20% | SDR | Hardness | Color | Clarity |
|---|---|---|---|---|---|---|
| $100_T50_S$ | 100 ml | 50 ml | 850 ml | F | Yellow | X |
| $100_T0_S$ | 100 ml | 0 ml | 900 ml | S | colorless | X |
| $50_T50_S$ | 50 ml | 50 ml | 900 ml | S | colorless | X |
| $50_T0_S$ | 50 ml | 0 ml | 950 ml | F | Pale yellow | L |
| $25_T25_S$ | 25 ml | 25 ml | 950 ml | S | colorless | L' |
| $25_T0_S$ | 25 ml | 0 ml | 975 ml | S | colorless | L |
| $0_T25_S$ | 0 ml | 25 ml | 975 ml | Liquid | colorless | L |
| Remarks | | SDS: Sodium dodecyl sulfate | SDR: Signal developing reagent | F: firm gel S: soft gel | | X: milky L: Clear L': Semi-milky |

*Tween 20 is a commercially available form of Polysorbate 20 - Tween is a Registered Trade Mark

Example 2

Preparation of the Iso-Propanol (IPA) Based Carrier Medium for FDA Amplification Procedure The IPA based carrier medium for FDA is composed of IPA, NaOH and polyvinylpyrrolidone (PVP), in which the purpose of the IPA is to dissolve the FDA and NaOH is used to hydrolyse the dissolved FDA. PVP is used to increase the viscosity of the carrier medium. Specifically, the constituents are mixed together (e.g., mixing 1 ml of IPA+1 ml of 1M NaOH+0.2 g of PVP).

Example 3

Application of Carrier Medium on Microtitre-Plate Based Test

1 µg of Gt-α-MIgG was coated as a dot on a nylon membrane placed inside each well of a microtitre plate by means of a microsyringe pump with a diameter of 1 mm. The plate was then dried under vacuum for 2 hours. After that, the plate was washed by a washing buffer [10 mM PBS, 0.1% (w/v) BSA, 0.5% (w/v) Polysorbate-20] 5 times. The wells were then blocked with 100 µl of 1% of BSA solution at 37° C. for 30 minutes. 25 µL of MIgG (100 µg/L) and 25 µL of biotin-Gt-α-MIgG were added to each well and incubated at 37° C. for 1 hour. After 5 washing cycles, avidin conjugated with FDA nanocrystals was added to each well and incubated again at 37° C. for 1 hour. After 5 washing cycles, the carrier medium as described in Example 2 was added to each well. A fluorescent dot was observed instantly under a UV light. This scheme was described above with reference to FIG. 5 for multi-target detection.

The invention claimed is:

1. A lateral flow test device for detecting a target material in a fluid sample, said device comprising:
    a solid-phase substrate detection system comprising a porous membrane or a non-porous flat surface for transporting the fluid sample from a sample application site to a detection site;
    disposed at a position remote from said detection site, a non-catalytic label conjugated with a specific affinity molecule for the target material, said non-catalytic label comprising a plurality of signal precursor molecules, said signal precursor molecules being convertible to a plurality of detectable signal generating molecules;
    a carrier medium comprising a solvent for the dissolution of the non-catalytic label and a thickener for causing localization of signal generated by said plurality of detectable signal generating molecules at said detection site indicating the presence and/or quantity of said target material, and
    an optically transparent lid for placement over the test strip after completion of a reaction to detect target material;
    wherein said carrier medium is a continuous layer of gel located on the underside of said optically transparent lid and wherein said optically transparent lid is adapted to bring said continuous layer of gel into contact with said signal precursor molecules at least at said detection site.

2. The test device as claimed in claim 1 wherein the optically transparent lid is hinged to a back laminate for holding porous components of the device.

3. The test device as claimed in claim 1 further comprising a removable protective layer overlying the carrier medium.

4. The test device as claimed in claim 1 wherein the porous membrane is selected from the group consisting of nitrocellulose and nylon.

5. The test device as claimed in claim 1 wherein said affinity molecule is selected from the groups consisting of:
    (a) peptides or proteins selected from the group consisting of antibodies, genetically modified antibodies, monoclonal antibodies, polyclonal antibodies, receptors, antigens, lectins, avidins, oligopeptides, lipoproteins, glycoproteins, peptide hormones and allergens;
    (b) nucleic acids selected from the group consisting of DNA, RNAs, oligonucleotides and aptamers;
    (c) carbohydrates selected from the group consisting of mono-, oligo- and polysaccharides, glycolipids and proteo-polysaccharides; and
    (d) low molecular weight ligands selected from the group consisting of biotin, biotin derivatives, steroids, hormones, cofactors, activators, inhibitors, drugs, allergens and haptens.

6. The test device as claimed in claim 1 further comprising a signal developing reagent contained in said carrier medium for converting said plurality of signal precursor molecules to said plurality of detectable signal generating molecules.

7. The test device as claimed in claim 6 wherein said signal developing reagent is a base or esterase.

8. The test device as claimed in claim 1 wherein said signal precursor molecules are selected from the group consisting of fluorophores, luminophores, chromophores, prosthetic groups, redox active substances selected from the group consisting of redox mediators and electrode-active substances, bioluminogenic and fluorogenic proteins, visible dyes, fluorescent dyes, bioluminescent materials, chemiluminescent materials, electrochemically active materials, and magnetic materials.

9. The test device as claimed in claim 8 wherein the signal precursor molecules are fluorophores selected from the group consisting of fluoresceins and their derivatives, fluorescein diacetate (FDA), fluorescein diacetate isothiocyanate (FDA-isothiocyanate), fluorescein diacetate maleimide (FDA-maleimide), cyanines, carbocyanines, rhodamines, xanthenes, diazo-dye based fluorescent substances, and small fluorescent aromatic and heteroaromatic molecules.

10. The test device as claimed in claim 9 wherein said signal precursor molecules are selected from fluorescein diacetate (FDA), fluorescein diacetate isothiocyanate (FDA-isothiocyanate) and fluorescein diacetate maleimide (FDA-maleimide) and further comprising a signal developing reagent for the fluorescein diacetate (FDA), fluorescein diacetate Isothiocyanate (FDA-isothiocyanate) or fluorescein diacetate maleimide (FDA-maleimide).

11. The test device as claimed in claim 8 wherein the signal precursor molecules are fluorescein diacetate (FDA), and wherein the carrier medium comprises a solvent for FDA, a signal developing reagent and a thickener.

12. The test device as claimed in claim 11 wherein the solvent for FDA is dimethyl sulphoxide, the signal developing reagent is aqueous sodium hydroxide, and the thickener is Polysorbate 20.

13. The test device as claimed in claim 8 wherein the signal precursor molecules are chromophores selected from the group consisting of cyanine, pyrazolone, anthraquinone, carbocyanine, rhodamine, xanthen, carotenoid and diazo- and monoazo, oxazine, indigoid, and riboflavine based dye substances.

14. The test device as claimed in claim 1 wherein the proportion of thickener in the carrier medium ranges from 0.05 to 50% by weight based on the total weight of the carrier medium.

15. A test device of claim 1 wherein the non-porous flat surface is selected from the group consisting of glass, polystyrene, metal and carbon.

* * * * *